United States Patent
McLean

(10) Patent No.: US 10,433,981 B2
(45) Date of Patent: Oct. 8, 2019

(54) GRAFT DELIVERY APPARATUS

(71) Applicant: SPINE WAVE, INC., Shelton, CT (US)

(72) Inventor: Scott McLean, Sandy Hook, CT (US)

(73) Assignee: SPINE WAVE, INC., Shelton, CT (US)

( * ) Notice: Subject to any disclaimer, the term of this patent is extended or adjusted under 35 U.S.C. 154(b) by 255 days.

(21) Appl. No.: 15/491,434

(22) Filed: Apr. 19, 2017

(65) Prior Publication Data
US 2017/0325969 A1     Nov. 16, 2017

Related U.S. Application Data

(60) Provisional application No. 62/335,781, filed on May 13, 2016.

(51) Int. Cl.
*A61F 2/46*     (2006.01)
*A61F 2/44*     (2006.01)

(52) U.S. Cl.
CPC ............ *A61F 2/4601* (2013.01); *A61F 2/447* (2013.01); *A61F 2/4455* (2013.01); *A61F 2002/4475* (2013.01); *A61F 2002/4602* (2013.01)

(58) Field of Classification Search
CPC .. A61F 2/46; A61F 2/4601; A61F 2/44; A61F 2/447; A61F 2/4455
See application file for complete search history.

(56) References Cited

U.S. PATENT DOCUMENTS

| | | | |
|---|---|---|---|
| 4,800,875 | A | 1/1989 | Ray |
| 5,741,261 | A | 4/1998 | Moskovitz et al. |
| 8,308,805 | B2 | 11/2012 | Lynn et al. |
| 8,394,129 | B2 | 3/2013 | Morgenstern Lopez et al. |
| 8,425,612 | B2 | 4/2013 | Perez-Cruet et al. |
| 8,852,282 | B2 | 10/2014 | Farley et al. |
| 8,900,312 | B2 | 12/2014 | McLean et al. |
| 9,101,489 | B2 | 8/2015 | Protopsaltis et al. |
| 9,186,193 | B2 | 11/2015 | Kleiner et al. |
| 9,216,094 | B2 | 12/2015 | McLean et al. |
| 9,393,057 | B2 | 7/2016 | MacMillan et al. |
| 2008/0172128 | A1 | 7/2008 | Perez-Cruet et al. |
| 2012/0123548 | A1* | 5/2012 | Lynn ...................... A61F 2/442 623/17.16 |
| 2013/0006365 | A1 | 1/2013 | Pepper et al. |

(Continued)

*Primary Examiner* — Christopher J Beccia
(74) *Attorney, Agent, or Firm* — Hoffmann & Baron, LLP

(57) ABSTRACT

A system for delivering bone graft material during spinal interbody fusion comprises an interbody fusion device implanted in a spinal intradiscal space. The device has a distal end, a proximal end, opposing spaced side walls and opposing top and bottom surfaces defining a hollow interior. A channel extends through the proximal end in communication with the hollow interior. An elongate guide pin is releasably attached to the device proximal end. An elongate cannula has a first lumen extending therethrough, the cannula including a mating feature at a distal end releasably secured to the device to substantially align the first lumen with the device channel. The cannula includes an axially offset receiving member receiving the guide pin and an axially spaced retention member securing the cannula to the guide pin and the device. A tamp advances graft material in the first lumen into the device through the channel.

30 Claims, 4 Drawing Sheets

(56) References Cited

U.S. PATENT DOCUMENTS

| | | |
|---|---|---|
| 2013/0006366 A1 | 1/2013 | Farley et al. |
| 2015/0141964 A1* | 5/2015 | MacMillan ........ A61B 17/7094 604/522 |
| 2016/0106551 A1 | 4/2016 | Grimberg, Jr. et al. |
| 2016/0228261 A1 | 8/2016 | Emery et al. |

* cited by examiner

GRAFT DELIVERY APPARATUS

This application claims the benefit of U.S. Provisional Patent Application No. 62/335,781, filed May 13, 2016, the entire contents of which are incorporated by reference herein.

BACKGROUND OF THE INVENTION

Interbody fusion devices are well known in the prior art, including expandable interbody fusion devices and fixed-height interbody fusion devices. Examples of expandable interbody fusion devices may be found in U.S. Pat. No. 8,900,312 and in U.S. Pat. No. 9,216,094, both assigned to the assignee herein, and both which are incorporated by reference herein in their entireties. Further examples of expandable interbody fusion devices are found in devices sold by Spine Wave, Inc., of Shelton, Conn., U.S.A., under the brand name "VELOCITY".

As is well known with techniques relating to implantation of interbody fusion devices, bone graft material is typically introduced in and about an implanted device to foster bone fusion between target vertebrae. Various techniques are known in the prior art for introducing graft material intradiscally. One example is described in U.S. Pat. No. 5,741,261, which issued to Moskovitz et al. on Apr. 21, 1998, wherein a graft delivery apparatus comprises a delivery cannula having a funnel at the introduction end. A quantity of bone graft material is received in the cannula and a delivery piston is provided for insertion into the cannula to manually eject graft material from the cannula to the fusion site. Other graft delivery systems are known, such as the system described in U.S. Pat. No. 9,186,193, which issued to Kleiner et al. on Nov. 17, 2015, wherein a graft delivery device is integrated with a fusion cage to disperse biologic material through the cage to a disc space.

SUMMARY OF THE INVENTION

A graft delivery apparatus is provided herein for delivering graft material into an implant such as an interbody fusion device, particularly after implantation of the implant into an intradiscal space of a spine. The apparatus, in a broadest aspect, generally includes a cannula having a first lumen extending therethrough. The cannula includes mating features for releasably securing the cannula to the implant in a manner that substantially aligns the first lumen to a channel formed through a proximal end of the implant. The mating features of the cannula further include structure to receive a guide pin attached to the implant during insertion of the implant into the intradiscal space and to guide the cannula along the guide pin to the desired orientation relative to the implant. A retention feature secures the cannula to both the guide pin and the implant. A tamp is provided to be received in and through the first lumen to advance graft material placed in the first lumen into the implant.

DESCRIPTION OF THE DRAWING FIGURES

DETAILED DESCRIPTION

With reference to the attached Figures, a bone graft delivery apparatus 10 is provided for delivering bone graft material into an intradiscal space, particularly after implantation of an interbody fusion device. The apparatus 10 may be utilized with various interbody fusion devices, including the expandable interbody fusion devices sold by Spine Wave, Inc. under the brand name "VELOCITY" described in U.S. Pat. No. 9,216,094, which issued to McLean et al. on Dec. 22, 2015 (the '094 patent"), as well as the expandable interbody fusion devices described in U.S. Pat. No. 8,900,312, which issued to McLean et al. on Dec. 2, 2014 (the '312 patent). The '094 patent and the '312 patent are incorporated herein by reference in their entireties.

Figure 1:
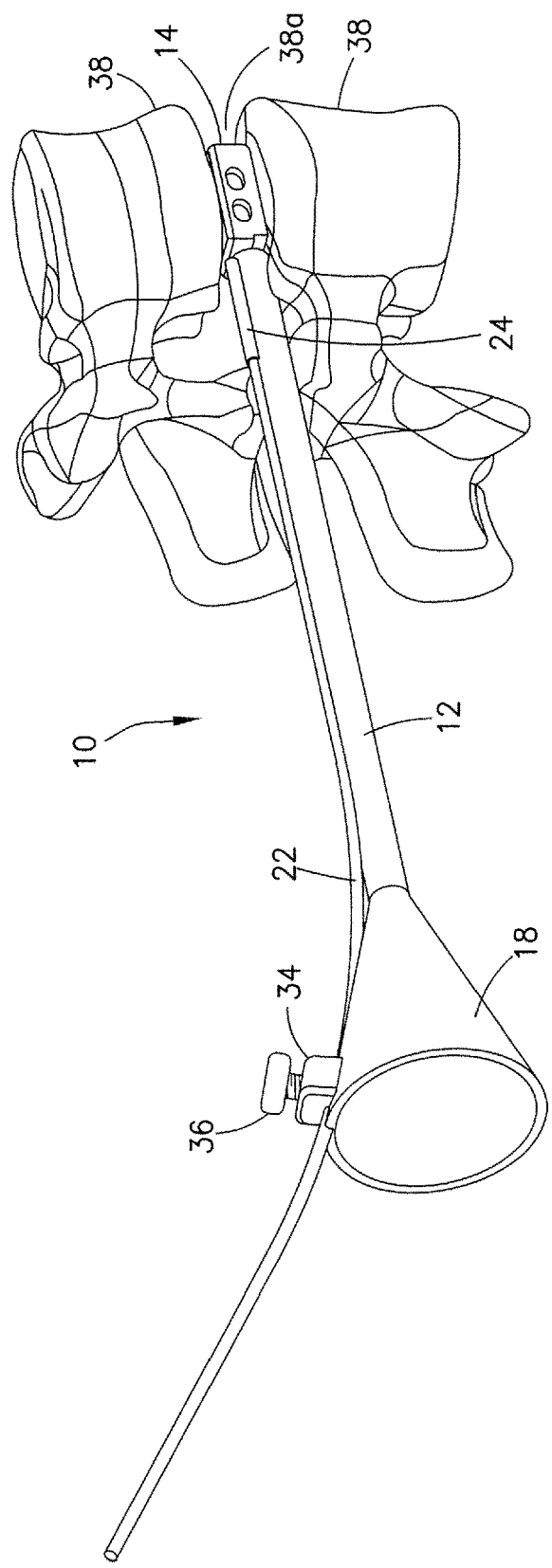
FIG. 1 is a perspective view of a graft delivery apparatus attached to an interbody fusion device inserted into an intradiscal space of a spine.
Figure 2:
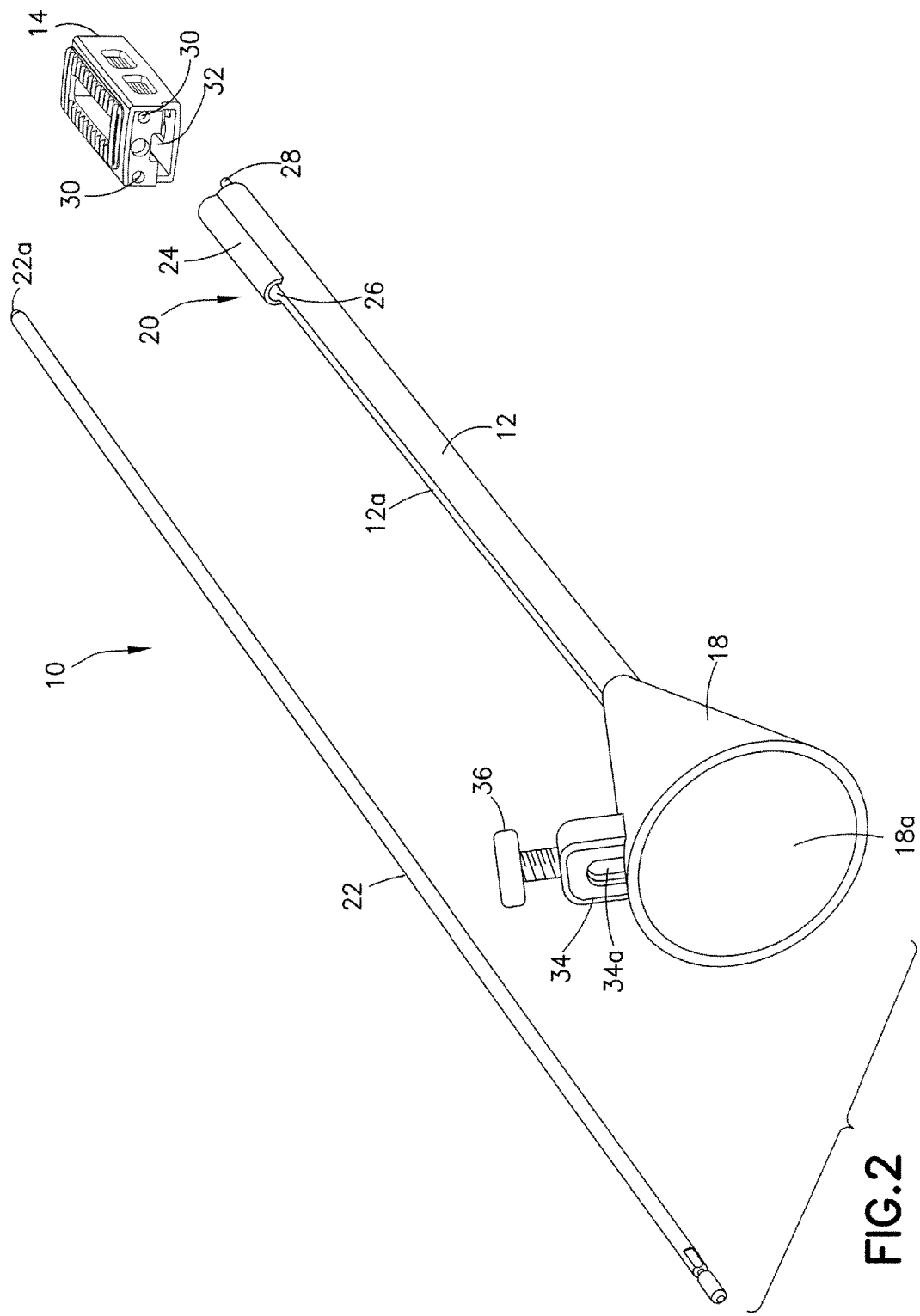
FIG. 2 is an exploded perspective view of the graft delivery apparatus of FIG. 1.
Figure 3:
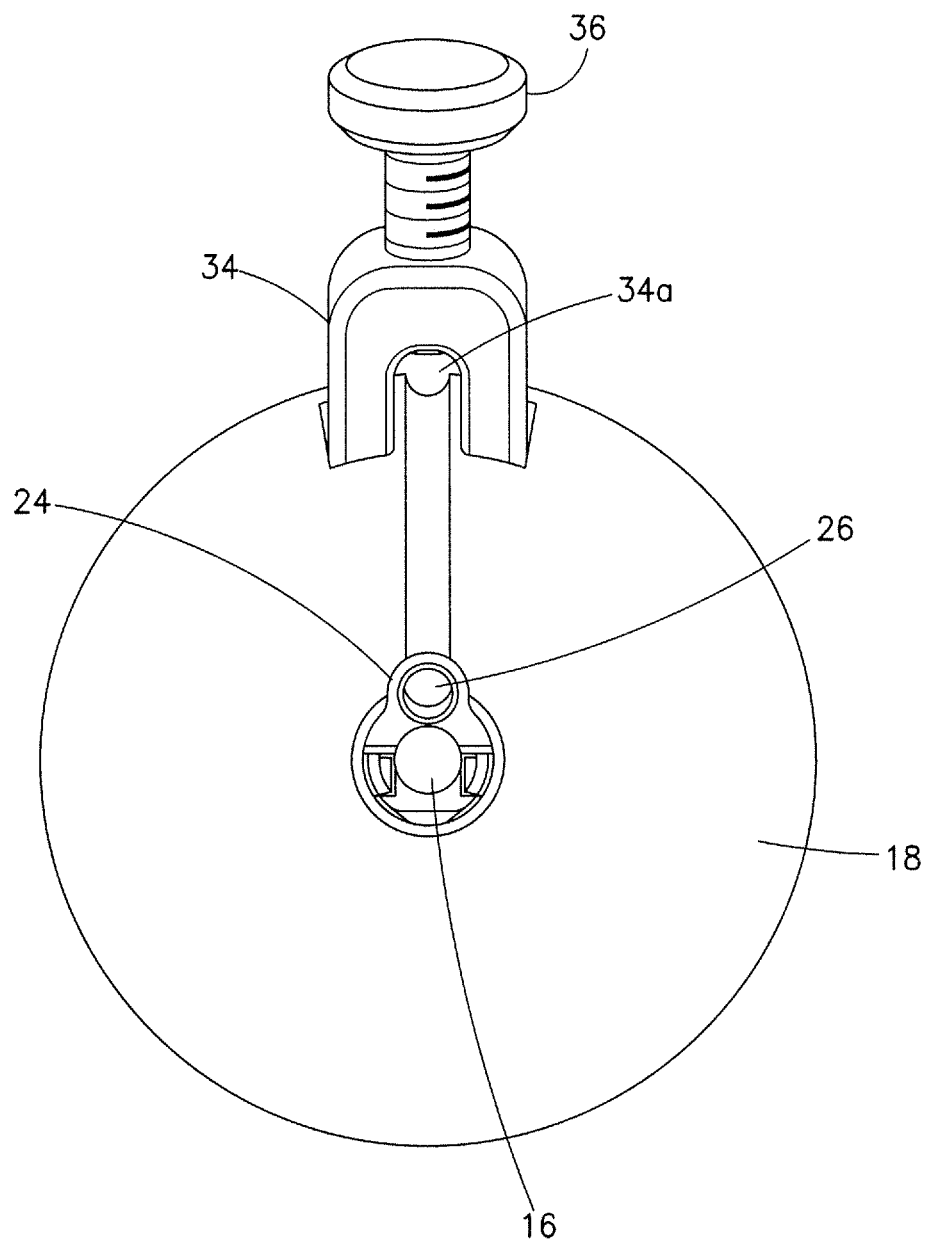
FIG. 3 is an elevation view of the proximal end of the cannula of the graft delivery apparatus of FIG. 2.

The graft delivery apparatus 10 as shown in FIGS. 1-3 includes an elongated cannula 12 releasably attached to the proximal end of spinal implant 14. Spinal implant 14 may be an expandable interbody fusion device 14, described in more detail in the '094 patent. Cannula 12 defines a first lumen 16 extending through the length of cannula 12. The proximal end of cannula 12 is provided with a funnel 18 having an enlarged flared internal opening 18a in communication with first lumen 16 to facilitate the introduction of bone graft material into and through first lumen 16.

Cannula 12 is further provided with one or more mating features 20 for releasably attaching cannula 12 to the proximal end of implant 14 and to a guide pin 22. Mating features 20 may include a channel 24 that defines a second lumen 26, channel 24 being formed adjacent the distal end of cannula 12 and extending for an extent partially along the length of cannula 12. In a particular arrangement second lumen 26 is fully bounded by channel 24 and is disposed substantially parallel to and axially offset from first lumen 16. Second lumen 26 is configured and sized to receive guide pin 22, as will be described further. Second lumen 26 may also be formed as an open slot or other configuration to receive guide pin 22 in a manner to releasably mate with cannula 12 and to guide cannula 12 along guide pin 22.

Further formed at the distal end of cannula 12 are a pair of substantially diametrically opposed axially extending tabs 28 that are configured and sized to extend into notches or openings 30 formed on the proximal end of implant 14. The positioning of tabs 28 into openings 30 serves to orient cannula 12 on implant 14 and to prevent rotation of cannula 12 relative to implant 14. Cannula 12 is oriented such that first lumen 16 is substantially aligned with and communicates with channel 32 formed through the proximal end of implant 14 and in communication with the interior of implant 14. Formed at the proximal end of cannula 12, which may be located on and integrated with funnel 18, is a guide pin retention bracket 34. Bracket 34 defines an opening 34a for receipt of the proximal end of guide pin 22. A retention screw 36 is threadably supported by bracket 34 to engage and secure guide pin 22 and to secure cannula 12 to implant 14. A slot 12a may be formed into cannula 12 along its length between channel 24 and the distal end of funnel 18, slot 12a defining a track within which guide pin 22 may be at least partially contained so as to support guide pin 20 in a relatively fixed position on cannula 12.

Use of graft delivery apparatus is now described. Implant 14 is inserted into the intradiscal space 38a between two opposed vertebral bodies 38 of the spine, as shown in FIG. 1. Implant insertion is effected with use of an inserter instrument as more fully described in the '094 patent. Such inserter instrument is releasably attached to the proximal end of implant 14 and comprises guide pin 22. Guide pin 22 is releasably attached to implant 14, for example by threaded end 22a at the distal end of guide pin 22, and is also detachably connected to the inserter instrument. As such, inserter instrument may be removed from both implant 14 as well as guide pin 22 after insertion of implant 14 into the intradiscal space, while guide pin 22 remains attached to implant 14. The maintenance of the connection of guide pin 22 to implant 14 provides a surgeon with good visualization to the surgical site as well as good fluoroscopic imaging of the implant position without losing a secure connection to the implant 14. As the guide pin 22 projects out from the tissue of the patient it also provides a path to guide additional instruments to the implant 14 at a defined location.

Figure 4:
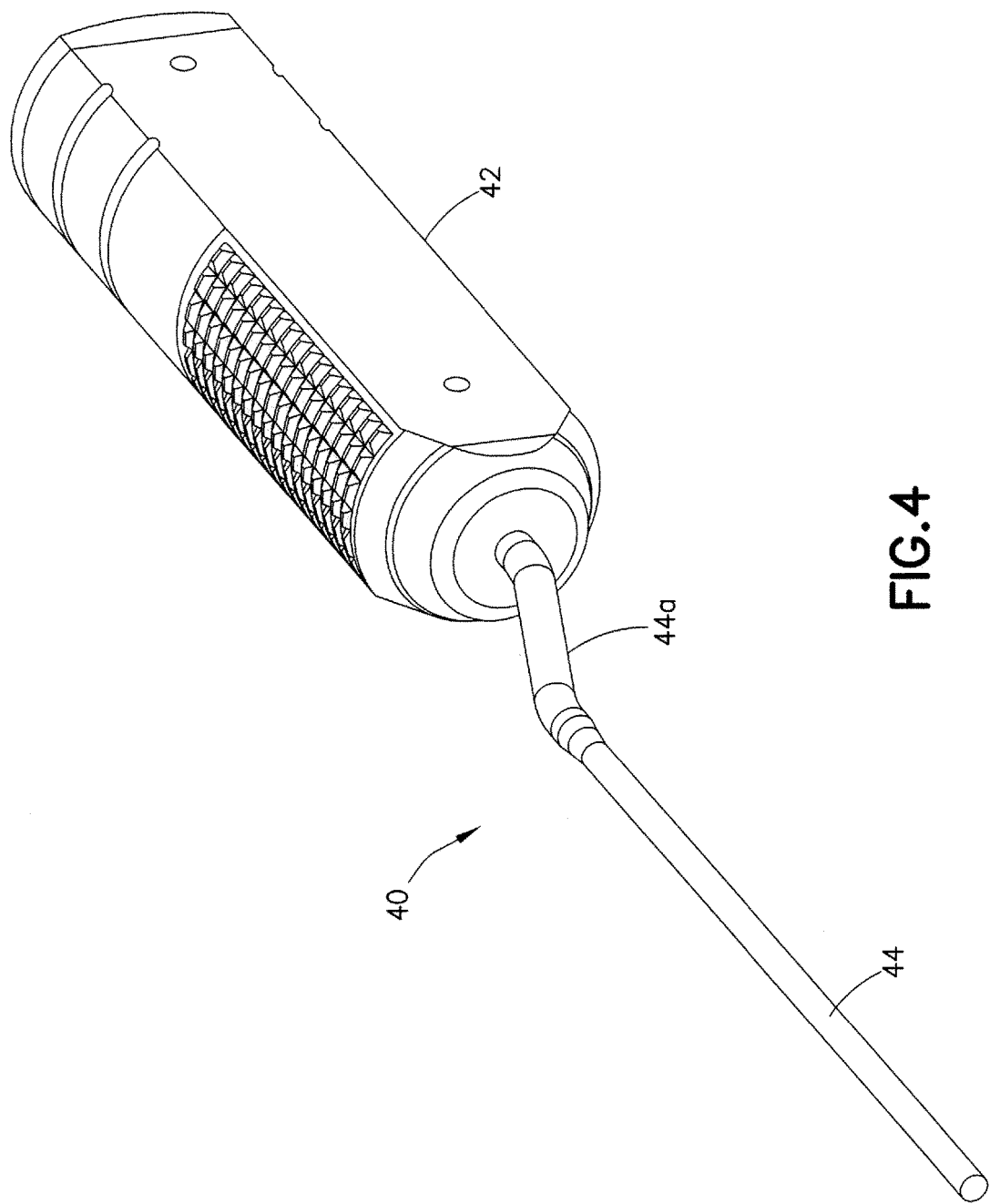
FIG. 4 is a perspective view of a tamp for use with the graft delivery apparatus of the subject invention.

The cannula 12 is then placed onto guide pin 22 whereby second lumen 26 receives guide pin 22 and guides cannula 12 toward implant 14. Upon continued movement of cannula 12 along guide pin 22, guide pin 22 will slide within track 12a until the proximal end of guide pin 22 is fed through opening 34a of bracket 34. Final movement of cannula 12 along guide pin 22 results in the introduction of tabs 28 into openings 30 in the proximal end of implant 14. Tightening of retention screw 36 substantially locks cannula 12 to guide pin 22 and to implant 14. In this position, first lumen 16 is substantially aligned with and communicates with channel 32 in implant 14 thereby creating a direct path for graft material to flow through cannula 12 and into implant 14 to fill graft chambers provided in implant 14. The length of cannula 12 may be less than the length of guide pin 22 such that the proximal end of guide pin 22 may be deflected by funnel 18 and attached at bracket 34. As shown in FIG. 4, a tamp 40 or other delivery piston may be provided to manually advance graft material through cannula 12 into implant 14. Tamp 40 includes a handle 42 supporting and elongate shaft 44 that is configured and sized to be received in first lumen 16 of cannula 12. Shaft 44 may have an offset portion 44a to for better visualization of tamp 40 in use.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A system for delivering bone graft material during spinal interbody fusion, comprising;
    an interbody fusion device implanted in an intradiscal space of a spine, said interbody fusion device having a distal end and a proximal end, opposing spaced side walls and opposing top and bottom surfaces defining a hollow interior, and a channel extending through said proximal end in communication with said hollow interior;
    an elongate guide pin having a distal end and a proximal end, said distal end being releasably attached to the proximal end of said device;
    an elongate cannula having a distal end and a proximal end and a first lumen extending therethrough, said cannula including a mating feature at the distal end releasably secured to the proximal end of said device in a manner that substantially aligns said first lumen with said channel formed through the proximal end of the device, said cannula including a receiving member axially offset from said first lumen in receipt of said guide pin, said cannula including a retention member configured to receive said guide pin and to secure said guide pin to said cannula and said device; and
    a tamp having a portion sized and configured to be received in and through the first lumen to advance graft material in said first lumen into said device.

2. The system of claim 1, wherein said receiving member defines a second lumen extending at least partially along the length of said cannula.

3. The system of claim 2, wherein said receiving member is a guide pin channel defining said second lumen.

4. The system of claim 3, wherein said second lumen is fully bounded by said guide pin channel and is substantially parallel to said first lumen.

5. The system of claim 3, wherein said guide pin channel is disposed adjacent said distal end of said cannula.

6. The system of claim 5, wherein said device includes at least one opening in the proximal end thereof, and said mating feature of said cannula includes at least one tab projecting from the distal end of said cannula and extending into said at least one opening.

7. The system of claim 6, wherein said device includes two spaced openings in the proximal end thereof, one opening being disposed on either side of said channel in the proximal end of said device, and wherein said cannula includes two tabs substantially diametrically opposed, one on either side of said first lumen, each tab extending into a respective opening in the proximal end of said device.

8. The system of claim 6, wherein the distal end of said guide pin includes a threaded extent, said threaded extent being in threaded attachment to the proximal end of said device.

9. The system of claim 6, wherein said retention member is axially spaced from said mating feature and includes a bracket having an opening in receipt of said proximal end of said guide pin.

10. The system of claim 9, wherein said retention member is disposed adjacent said proximal end of said cannula.

11. A system for delivering bone graft material during spinal interbody fusion, comprising:
    an interbody fusion device implanted in an intradiscal space of a spine, said interbody fusion device having a distal end and a proximal end, opposing spaced side walls and opposing top and bottom surfaces defining a hollow interior, and a channel extending through said proximal end in communication with said hollow interior;
    an elongate guide pin having a distal end and a proximal end, said distal end being releasably attached to the proximal end of said device;
    an elongate cannula having a distal end and a proximal end and a first lumen extending therethrough, said cannula including a mating feature at the distal end releasably secured to the proximal end of said device in a manner that substantially aligns said first lumen with said channel formed through the proximal end of the device, said cannula including a receiving member axially offset from said first lumen in receipt of said guide pin, said cannula including a retention member securing said cannula to said guide pin and said device, said retention member comprising a bracket having an opening in receipt of said proximal end of said guide pin; and
    a tamp having a portion sized and configured to be received in and through the first lumen to advance graft material in said first lumen into said device.

12. The system of claim 11, wherein said bracket supports a retention screw communicating with said bracket opening and securing said guide pin to said cannula.

13. The system of claim 11, wherein said cannula includes at the proximal end thereof a funnel having a distal end and a proximal end, said funnel having an enlarged internal opening in communication with said first lumen and flaring outwardly toward the proximal end of said funnel.

14. The system of claim 13, wherein said cannula includes a track extending axially on said cannula between said guide pin channel and said funnel.

15. The system of claim 14, wherein said track is defined by a slot formed into said cannula.

16. The system of claim 13, wherein said retention member is located on said funnel.

17. The system of claim 16 wherein said cannula has a length less than a length of said guide pin.

18. The system of claim 11, wherein said tamp includes a handle, and wherein said tamp portion is an elongate shaft attached to said handle.

19. The system of claim 18, wherein said elongate shaft includes an extent that is axially offset relative to said handle.

20. An apparatus for delivering bone graft material during spinal interbody fusion, comprising:
an elongate cannula having a distal end and a proximal end and a first lumen extending therethrough, said cannula including a mating feature at the distal end for releasably securing the cannula to an interbody fusion device implanted in an intradiscal space, said cannula including a receiving member axially offset from said first lumen for receipt of a guide pin attached to said interbody fusion device, said cannula including a retention member for securing said cannula to said guide pin and said device, said retention member comprising a bracket having an opening for receipt of said guide pin.

21. The apparatus of claim 20, wherein said receiving member defines a second lumen extending at least partially along the length of said cannula.

22. The apparatus of claim 21, wherein said receiving member is a guide pin channel defining said second lumen.

23. The apparatus of claim 22, wherein said second lumen is fully bounded by said guide pin channel and is substantially parallel to said first lumen.

24. The apparatus of claim 22, wherein said guide pin channel is disposed adjacent said distal end of said cannula.

25. The apparatus of claim 24 wherein said retention member is axially spaced from said mating feature.

26. The apparatus of claim 25, wherein said retention member is disposed adjacent said proximal end of said cannula.

27. The apparatus of claim 20, wherein said bracket supports a retention screw communicating with said bracket opening for securing said guide pin to said cannula.

28. The apparatus of claim 27, wherein said cannula includes at the proximal end thereof a funnel having a distal end and a proximal end, said funnel having an enlarged internal opening in communication with said first lumen and flaring outwardly toward the proximal end of said funnel.

29. The apparatus of claim 28, wherein said cannula includes a track extending axially on said cannula between said guide pin channel and the distal end of said funnel.

30. The apparatus of claim 29, wherein said track is defined by a slot formed into said cannula.

* * * * *